United States Patent
Iyengar et al.

(10) Patent No.: US 12,144,616 B2
(45) Date of Patent: *Nov. 19, 2024

(54) EYEWEAR WITH BLOOD SUGAR DETECTION

(71) Applicant: Snap Inc., Santa Monica, CA (US)

(72) Inventors: Venu Iyengar, Fremont, CA (US); Russell Douglas Patton, Playa Vista, CA (US)

(73) Assignee: Snap Inc., Santa Monica, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 18/201,008

(22) Filed: May 23, 2023

(65) Prior Publication Data

US 2023/0293061 A1 Sep. 21, 2023

Related U.S. Application Data

(63) Continuation of application No. 16/833,959, filed on Mar. 30, 2020, now Pat. No. 11,690,539.

(51) Int. Cl.
*A61B 5/145* (2006.01)
*A61B 5/00* (2006.01)
*A61B 5/16* (2006.01)
*G02C 1/08* (2006.01)

(52) U.S. Cl.
CPC ........ *A61B 5/14532* (2013.01); *A61B 5/0077* (2013.01); *A61B 5/163* (2017.08); *A61B 5/6803* (2013.01); *A61B 5/742* (2013.01); *G02C 1/08* (2013.01); *A61B 2560/04* (2013.01); *A61B 2562/02* (2013.01)

(58) Field of Classification Search
CPC ... A61B 5/14532; A61B 5/0077; A61B 5/163; A61B 5/6803; A61B 5/742; A61B 2560/04; A61B 2562/02; A61B 5/14555; G02C 1/08; G02C 11/04; G02C 11/10
See application file for complete search history.

(56) References Cited

U.S. PATENT DOCUMENTS

| | | | |
|---|---|---|---|
| 10,893,198 B1 * | 1/2021 | Zhang | H04N 23/60 |
| 11,690,539 B1 | 7/2023 | Iyengar et al. | |
| 2016/0174853 A1 * | 6/2016 | Cho | A61B 5/4261 600/301 |

* cited by examiner

*Primary Examiner* — Jay B Shah
*Assistant Examiner* — Meghan R Kumar
(74) *Attorney, Agent, or Firm* — CM Law; Stephen J. Weed (57) ABSTRACT

An eyewear device, method for use with an eyewear device, and a non-transient computer readable medium for detecting blood sugar levels are disclosed. The eyewear device has a frame including a first rim configured to support a first lens, a second rim configured to support a second lens, and a bridge connecting the first rim to the second rim. The bridge is configured to receive a nose of a user when the eyewear device is worn by the user. Blood sugar levels are detected by monitoring behavior of a pupil of an eye of the user with a sensor, comparing the monitored behavior with known blood sugar level behaviors, identifying a match responsive to the comparison between the monitored behavior and one of the known blood sugar level behaviors corresponding to a particular blood sugar level, and selecting the particular blood sugar level as a blood sugar level of the user.

20 Claims, 10 Drawing Sheets

EYEWEAR WITH BLOOD SUGAR DETECTION

CROSS-REFERENCE TO RELATED APPLICATIONS

This application is a Continuation of U.S. application Ser. No. 16/833,959 filed on Mar. 30, 2020, the contents of which are incorporated fully herein by reference.

TECHNICAL FIELD

The present subject matter relates to wearable devices, e.g., eyewear devices, for use in detecting blood sugar levels.

BACKGROUND

Wearable devices, including portable eyewear devices, such as smart glasses, headwear, and headgear, available today integrate electronic components. Technological improvements have led to wearable devices exhibiting improved comfort and usefulness.

Blood sugar levels represent the amount of sugar (glucose) present in the blood of a human. The body regulates blood sugar levels through the secretion of insulin in order to keep the body in homeostasis. The blood sugar level for a healthy person is typically between 72 mg/dL (3.8 to 4 mmol/L) and 108 mg/dL (5.8 to 6 mmol/L). Blood sugar levels outside of this range may be due to, for example, exercise, stress, or a medical condition.

BRIEF DESCRIPTION OF THE DRAWINGS

The drawing figures depict one or more implementations, by way of example only, not by way of limitations. In the figures, like reference numerals refer to the same or similar elements with a letter designation added to differentiate between the same or similar elements. The letter designation may be dropped when the same or similar elements are referred to collectively or when referring to a non-specific one of the same or similar elements.

DETAILED DESCRIPTION

Aspect of this disclosure relate to detecting blood sugar levels with an eyewear device. In an example, the eyewear device has a frame including a first rim configured to support a first lens, a second rim configured to support a second lens, and a bridge connecting the first rim to the second rim. The bridge is configured to receive a nose of a user when the eyewear device is worn by the user. Blood sugar levels are detected by monitoring behavior of a pupil of an eye of the user with a sensor, comparing the monitored behavior with known blood sugar level behaviors, identifying a match responsive to the comparison between the monitored behavior and one of the known blood sugar level behaviors corresponding to a particular blood sugar level, and selecting the particular blood sugar level as a blood sugar level of the user. The blood sugar level may be provided to the wearer via an alert or transmitted to a third party.

In the following detailed description, numerous specific details are set forth by way of examples in order to provide a thorough understanding of the relevant teachings. However, it should be apparent to those skilled in the art that the present teachings may be practiced without such details. In other instances, description of well-known methods, procedures, components, and circuitry are set forth at a relatively high-level, without detail, in order to avoid unnecessarily obscuring aspects of the present teachings.

The term "coupled" or "connected" as used herein refers to any logical, optical, physical or electrical connection, link or the like by which electrical or magnetic signals produced or supplied by one system element are imparted to another coupled or connected element. Unless described otherwise, coupled or connected elements or devices are not necessarily directly connected to one another and may be separated by intermediate components, elements or communication media that may modify, manipulate or carry the electrical signals. The term "on" means directly supported by an element or indirectly supported by the element through another element integrated into or supported by the element.

The orientations of the eyewear device, associated components and any complete devices such as shown in any of the drawings, are given by way of example only, for illustration and discussion purposes. In operation, the eyewear device may be oriented in any other direction suitable to the particular application of the eyewear device, for example up, down, sideways, or any other orientation. Also, to the extent used herein, any directional term, such as front, rear, inward, outward, toward, left, right, lateral, longitudinal, up, down, upper, lower, top, bottom, side, horizontal, vertical, and diagonal are used by way of example only, and are not limiting as to direction or orientation of any component described herein.

Objects, advantages and novel features of the examples will be set forth in part in the following description, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

Reference now is made in detail to the examples illustrated in the accompanying drawings and discussed below.

Figure 1A:
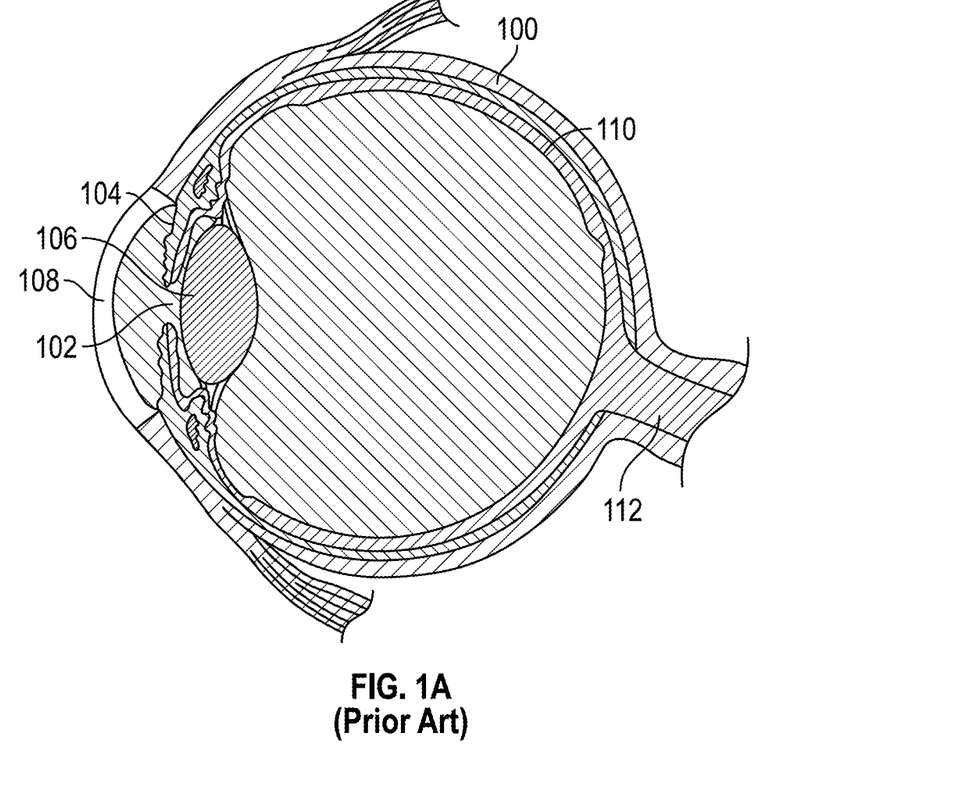
FIGS. 1A and 1B are side and front views, respectively, of a human eye in accordance with the prior art.
Figure 1B:
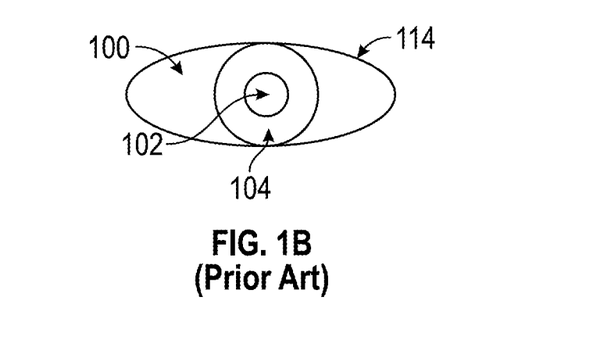

FIGS. 1A and 1B depict an eye 100 of a user of the eyewear device. The eye 100 includes a pupil 102 that enables light from a viewable scene to enter the eye 100. The size of the pupil 102 is defined by an iris 104 that responds to light levels entering the pupil and reaching a retina 110. In low light levels, the iris 104 contracts to increase the diameter of the pupil 102 (i.e., the pupil dilates) to let more light from the viewable scene into the eye 100. In higher light levels, the iris 104 expands to decrease the diameter of the pupil 102 (i.e., the pupil contracts) to reduce the amount of light entering the eye 100 to avoid damage to the eye 100. The eye 100 is positioned within a socket (not shown) and eyelids 114 cover at least a portion of the eye 100.

Light received by the eye 100 travels through a translucent cornea 106 and lens 108, which focuses the light on the retina 110. The light reaching the retina 110 forms an image of the viewable scene on a surface of the retina. The retina 110 produces signals from the image and the signals pass via the optic nerve 112 to the brain of the user for interpretation.

Blood sugar levels affect the behavior of the iris 104 and, thus, the pupil 102, e.g., its diameter/responsiveness. For example, when blood sugar is too low, the pupil tends to dilate. Additionally, when blood sugar is too high or too low, dilation/contraction may be erratic over time. Table 1 below provides example blood sugar levels corresponding to seven pupil behaviors.

TABLE 1

| Blood Sugar Level (BSL) | mg/dL | mmol/L | Pupil Behavior |
|---|---|---|---|
| Low | Less than 65 | Less than 3.6 | 1 |
| Normal optimal | 65-97 | 3.60-5.4 | 2 |
| Good marginal | 101-133 | 5.6-7.4 | 3 |
| At risk | 137-169 | 7.6-9.4 | 4 |
| Dangerously high | 172-205 | 9.6-11.4 | 5 |
| Possible complications | 208-240 | 11.6-13.4 | 6 |
| Mortal danger | Greater than 240 | Greater than 13.4 | 7 |

Figure 2A:
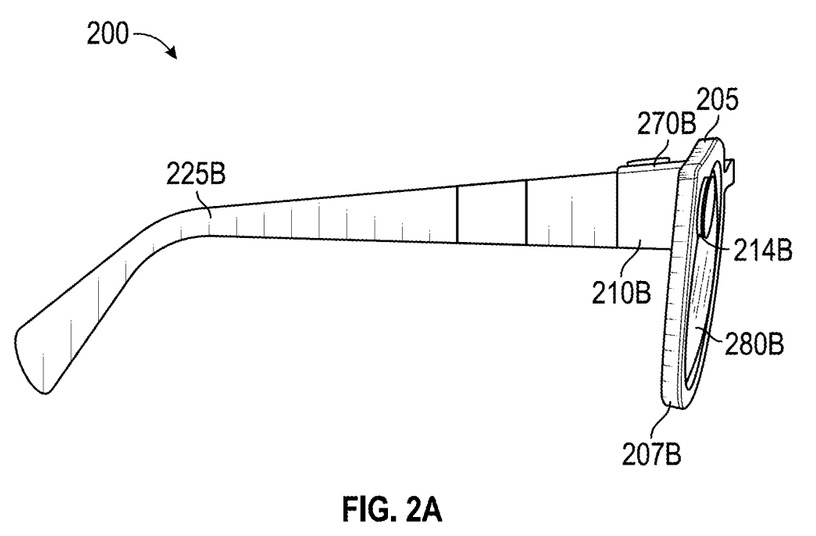
FIG. 2A is a side view of an example hardware configuration of an eyewear device, which shows a right optical assembly with an image display.

FIG. 2A is a side view of an example hardware configuration of an eyewear device 200, which includes a right optical assembly 280B with an image display. Eyewear device 200 includes multiple visible light cameras 214A-B that form a stereo camera, of which the right visible light camera 214B is located on a right corner 210B of the eyewear device 200.

The left and right visible light cameras 214A-B are sensitive to the visible light range wavelength. Examples of such visible lights camera 214A-B include a high-resolution complementary metal-oxide-semiconductor (CMOS) image sensor and a video graphic array (VGA) camera, such as 640p (e.g., 640×480 pixels for a total of 0.3 m 3 egapixels), 720p, or 1080p. Image sensor data from the visible light cameras 214A-B are captured along with geolocation data, digitized by an image processor, and stored in a memory.

To provide stereoscopic vision, visible light cameras 214A-B may be coupled to an image processor (element 612 of FIG. 6) for digital processing, including adding a timestamp of when the image of the scene is captured. Image processor 612 includes circuitry to receive signals from the visible light camera 214A-B and process those signals from the visible light camera 214 into a format suitable for storage in memory. A timestamp can be added by the image processor or other processor, which controls operation of the visible light cameras 214A-B. Visible light cameras 214A-B allow the stereo camera to simulate human binocular vision. The stereo camera provides the ability to reproduce three-dimensional images based on two captured images from the visible light cameras 214A-B having the same timestamp. Such three-dimensional images allow for an immersive life-like experience, e.g., for virtual reality or video gaming. For stereoscopic vision, a pair of images is generated at a given moment in time—one image for each of the left and right visible light cameras 214A-B. When the pair of generated images of the left and right visible light cameras 214A-B are stitched together (e.g., by the image processor), depth perception is provided by the optical assembly 280A-B.

The eyewear device 200 includes a frame 205, a right temple 225B extending from a right lateral side 270B of the frame 205, and an image display (e.g., optical assembly 280A-B) to present image overlays to a user. The eyewear device 200 includes a left visible light camera 214A connected to the frame 205 or the left temple 225A to capture a first image of the scene. Eyewear device 200 further includes a right visible light camera 214B connected to the frame 205 or the right temple 225B to capture (e.g., simultaneously with the left visible light camera 214A) a second image of the scene which partially overlaps the first image.

The frame 205 includes a left rim 207A connected to a right rim 207B via a bridge 206 adapted for a nose of the user when worn. The left and right rims 207A-B include respective apertures 275A-B which hold respective optical elements 280A-B, such as a lens and/or display devices. As used herein, the term lens is meant to cover transparent or translucent pieces of glass or plastic having curved and/or flat surfaces that cause light to converge/diverge or that cause little or no convergence or divergence.

Figure 2B:
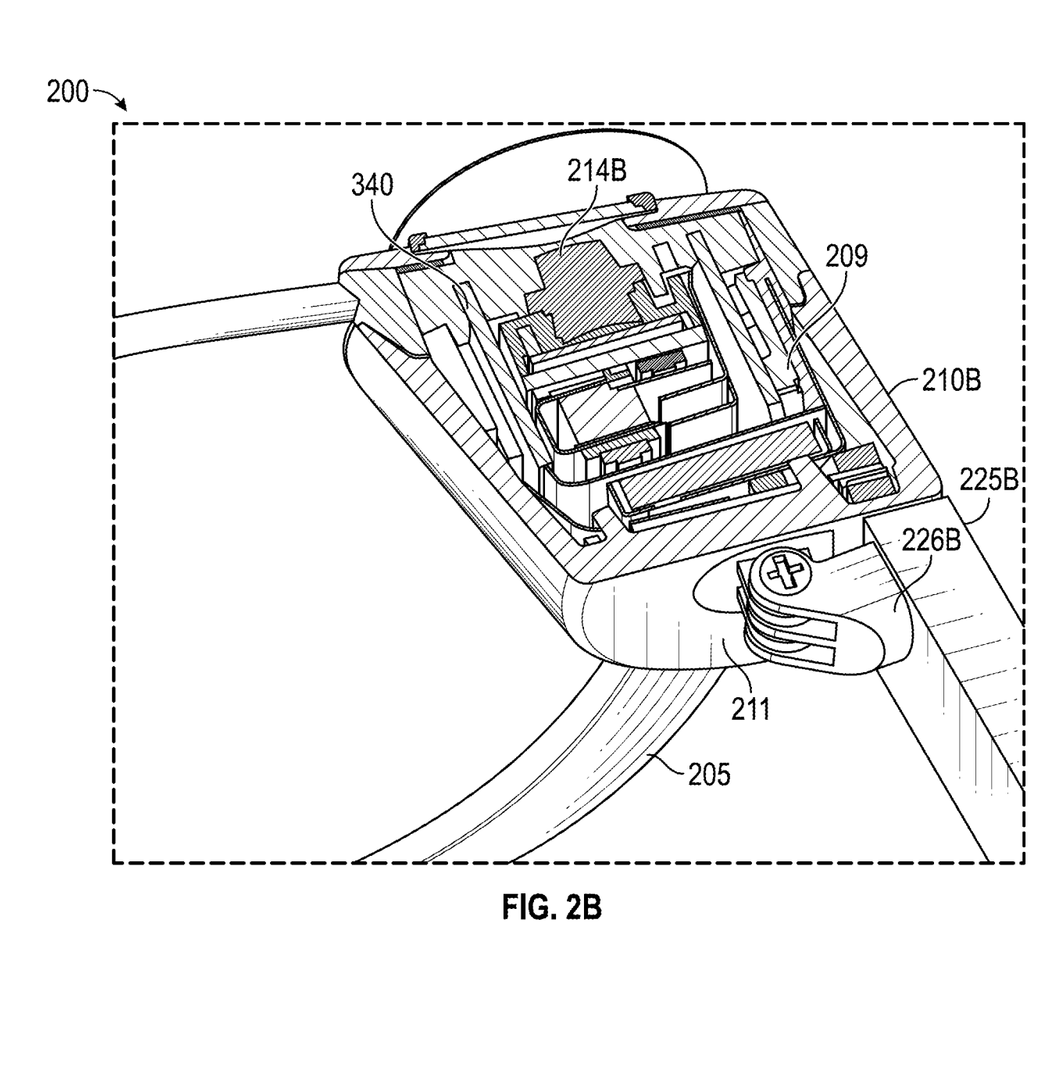
FIG. 2B is a top cross-sectional perspective view of a right corner of the eyewear device of FIG. 2A depicting a visible light camera, a head movement tracker for tracking the head movement of the user of the eyewear device, and a circuit board.
Figure 2C:
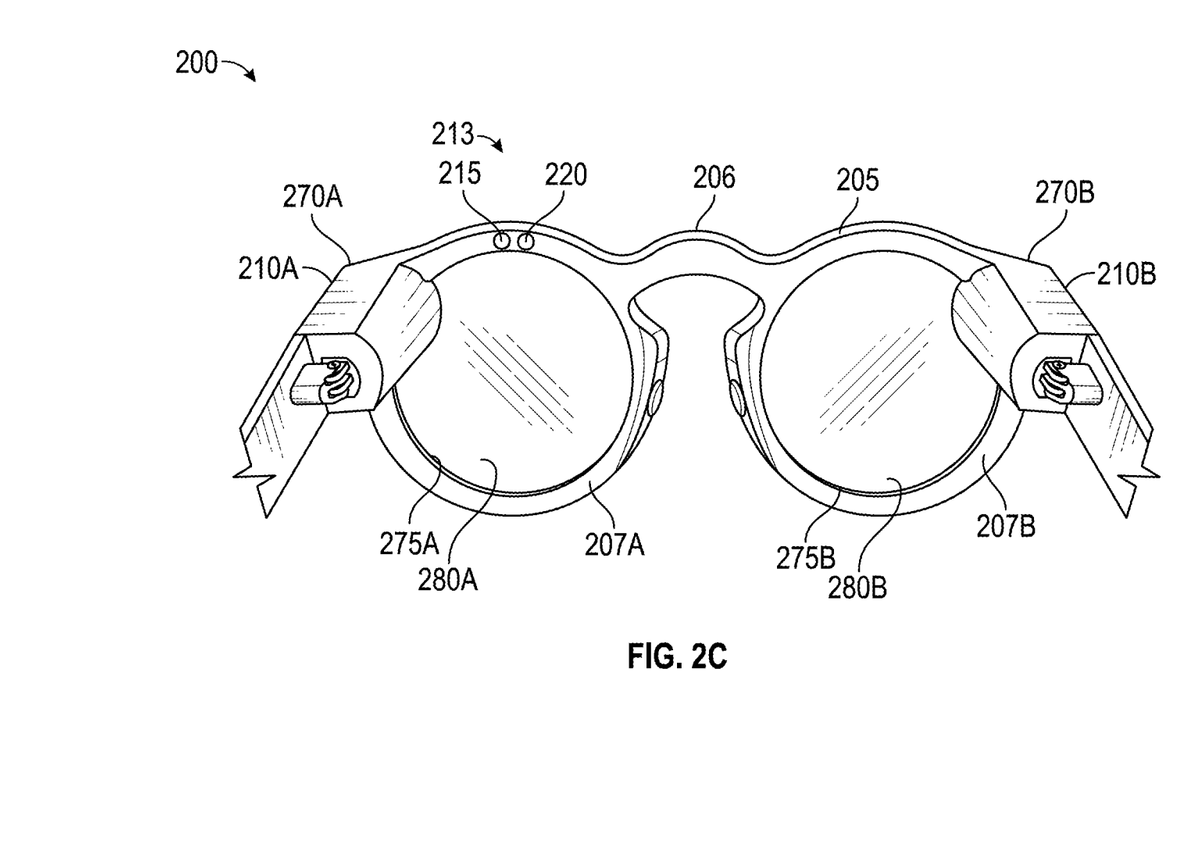
FIG. 2C is a rear view of the eyewear device of FIG. 2A depicting an illuminator and a sensor for sending blood sugar levels.

The eyewear device 200 may include a head movement tracker (element 209 of FIG. 2B) in addition to blood sugar level sensor (element 213 of FIG. 2C). Eyewear device 200 further includes the image display of optical assembly 280A-B for presenting a sequence of displayed images and an image display driver (element 642 of FIG. 6) coupled to the image display of optical assembly 280A-B to control the image display of optical assembly 280A-B to present the sequence of displayed images, which are described in further detail below. Eyewear device 200 further includes a memory (element 634 of FIG. 6) and a processor (element 643 of FIG. 6) having access to the image display driver (element 642 of FIG. 6) and the memory (element 634 of FIG. 6). Eyewear device 200 further includes programming in the memory.

Execution of the programming by the processor (element 643 of FIG. 6) configures the eyewear device 200 to perform functions, including functions to monitor pupil behavior (programming 601 of FIG. 6), compare monitored behavior to known blood sugar level behaviors (programming 602 of FIG. 6), identify a match between the monitored behavior and one of the known blood sugar levels corresponding to a particular blood sugar level (programming 603 of FIG. 6), select the particular blood sugar level at the blood sugar level for the user (programming 604 of FIG. 6), and alert a user and/or third party based on the selected blood sugar level (programming 605 of FIG. 6), e.g., via the image display 642. Execution of the programming by the processor (element 643 of FIG. 6) further configures the eyewear device 200 to present, via the image display of the optical assembly 280A-B, image overlays for alerting the user and/or to transmit alerts, via wireless circuitry, to third parties such as a parent or caregiver.

The right corner 210B includes corner body 211 and a corner cap, with the corner cap omitted in the cross-section of FIG. 2B. Disposed inside the right corner 210B are various interconnected circuit boards, such as PCBs or flexible PCBs, that include controller circuits for right visible light camera 214B, microphone(s), low-power wireless circuitry (e.g., for wireless short range network communication via Bluetooth™), high-speed wireless circuitry (e.g., for wireless local area network communication via WiFi).

The right visible light camera 214B is coupled to or disposed on the flexible PCB 240 and covered by a visible light camera cover lens, which is aimed through opening(s) formed in the right corner 210B. In some examples, the frame 205 connected to the right corner 210B includes the opening(s) for the visible light camera cover lens. The frame 205 includes a front-facing side facing outward away from the eye of the user. The opening for the visible light camera cover lens is formed on and through the front-facing side. In the example, the right visible light camera 214B has an outward facing angle of coverage 111B with a line of sight or perspective of the right eye of the user of the eyewear device 200. The visible light camera cover lens can also be adhered to an outward facing surface of the right corner 210B in which an opening is formed with an outward facing angle of coverage, but in a different outwards direction. The coupling can also be indirect via intervening components.

Left (first) visible light camera 214A is connected to a first image display of left optical assembly 280A to generate a first background scene of a first successive displayed image. Right (second) visible light camera 214B is connected to a second image display of right optical assembly 280B to generate a second background scene of a second successive displayed image. The first background scene and the second background scene partially overlap to present a three-dimensional observable area of the successive displayed image.

Flexible PCB 340 is disposed inside the right corner 210B and is coupled to one or more other components housed in the right corner 210B. Although shown as being formed on the circuit boards of the right corner 210B, the right visible light camera 214B can be formed on the circuit boards of the left corner 210A, the temples 125A-B, or frame 205.

FIG. 2C is a rear view of an example hardware configuration of an eyewear device 200, which includes a blood sugar level sensor 213 on a frame 205, for tracking the pupil of the eye of the user of the eyewear device 200. As shown in FIG. 2C, the eyewear device 200 is in a form configured for wearing by a user, which are eyeglasses in the example. The eyewear device 200 can take other forms and may incorporate other types of frameworks, for example, a headgear, a headset, or a helmet.

Although shown as having two optical elements 280A-B, the eyewear device 200 can include other arrangements, such as a single optical element or may not include any optical element 180A-B depending on the application or intended user of the eyewear device 200. As further shown, eyewear device 200 includes a left corner 210A adjacent the left lateral side 270A of the frame 205 and a right corner 210B adjacent the right lateral side 270B of the frame 205. The corners 210A-B may be integrated into the frame 205 on the respective sides 170A-B (as illustrated) or implemented as separate components attached to the frame 205 on the respective sides 270A-B. Alternatively, the corners 210A-B may be integrated into temples (not shown) attached to the frame 205.

In the example of FIG. 2C, the blood sugar level sensor 213 of the eyewear device 200 includes a camera 220 and an optional illuminator 215. Visible light cameras typically include a blue light filter to block infrared light detection, in an example, the camera 220 is a visible light camera, such as a low resolution video graphic array (VGA) camera (e.g., 640×480 pixels for a total of 0.3 megapixels), with the blue filter removed. The illuminator 215 may be an infrared light emitting diode (LED). Alternatively, the illuminator 215 may be another type of light source such as a visible light LED configured to initiate a pupil response (e.g., purple (437 nm), blue (479 nm), red (627 nm)), a light source configured to emit both infrared and visible light, or a separate infrared light source and visible light source.

In FIG. 2C, the illuminator 215 and the camera 220 are co-located on the frame 205, for example, both are shown as connected to the upper portion of the left rim 207A. As described in further detail below, the frame 205 or one or more of the left and right corners 210A-B include a circuit board that includes the illuminator 215 and the camera 220. The illuminator 215 and the camera 220 can be connected to the circuit board by soldering, for example. Other arrangements of the illuminator 215 and camera 220 can be implemented, including arrangements in which the illuminator 215 and camera 220 are both on the left rim 207A, or in different locations on the frame 205.

The illuminator 215 and camera 220 are arranged to face inwards towards the eye of the user with a partial or full angle of coverage of the eye in order to pick up an infrared image of the pupil of the eye to monitor pupil behavior. For example, the illuminator 215 and camera 220 are positioned directly in front of the eye, in the upper part of the frame 205 or in the corners 210A-B at either ends of the frame 205.

Blood sugar level sensors 213 can track pupil changes over time for comparison to know pupil behavior associated with blood sugar levels. For example, by comparing currently captured images to previously captured images associated with blood sugar levels. Blood sugar level sensor 213 may non-invasively measure pupil size changes utilizing video images of the eye over time with or without stimulus from illuminator 215. As noted above, a pattern of infrared light may be emitted by the illuminator 215 and infrared light reflected back from the eye with variations is sensed and imaged by a video camera, such as camera 220. Data forming the picked up infrared image is then analyzed to extract pupil diameter information and/or responsiveness of the pupil over time.

In one example, the illuminator 215 of the blood sugar level sensor 213 emits light to illuminate the user's eye, which can be infrared light (e.g., near-infrared, short-wavelength infrared, mid-wavelength infrared, long-wavelength infrared, or far infrared) or other short-wavelength beam of low-energy radiation. Alternatively, or additionally, the blood sugar level sensor 213 may include an illuminator that emits other wavelengths of light besides infrared and the blood sugar level sensor 213 further includes a camera sensitive to that wavelength that receives and captures images with that wavelength. For example, the blood sugar level sensor 213 may comprise a visible light camera that captures light in the visible light range from the eye, such as a red, green, and blue (RGB) camera.

Figure 2D:
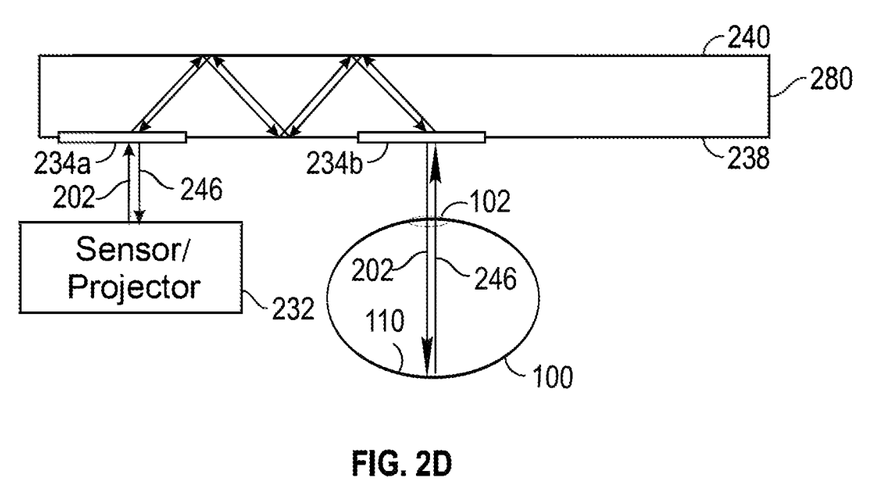
FIG. 2D is a block diagram of a waveguide within an optical element of the eyewear device of FIG. 2A.

In another example, the image display device of optical assembly 280A-B includes a projector/sensor 232 as shown in FIG. 2D. The projector/sensor 232 projects a beam of light 202 having a first circular polarization (e.g., p/s) toward a first coupling element 234a (e.g., a diffractive grating) that couples the light into a waveguide defined by a first surface 238 and a second surface 240 of an optical element 280. The first coupling element 234a redirects the light 202 into the waveguide, where it is internally reflected until it encounters a second coupling element 234b (e.g., another diffractive grating) that causes the light 202 to exit the waveguide toward the pupil 102 of an eye 100 of a user.

The light 202 enters the eye 100 through the pupil 102 and is reflected by the retina 110. The reflection by the retina 110 reverses the polarization such that the reflected light 246 has a second circular polarization (e.g., s/p) as it exits the eye 100 toward the second coupling element 234b that couples the light into the waveguide. The second coupling element 234a redirects the light 202 into the waveguide, where it is internally reflected until it encounters the first coupling element 234a that causes the light 202 to exit the waveguide toward the selector/projector 232. Due to the reverse polarization, a beam splitter within the selector/projector 232 may be used to direct the light 246 toward an imager such as a charge coupled device (CCD) array.

The light 202 entering the eye 100 forms a spot on the retina 110 that acts as a point light source. The point light source results in a beam 246 having a cross-section that is representative of the diameter of the pupil 102 as it exits the eye 100. Thus, the imager within the projector/sensor 232 can produce an output representing the diameter of the pupil 102 responsive to the beam 246 exiting the eye 100 and passing through the waveguide.

A pupil comparator (see element 602 of FIG. 6) including a database of pupil behaviors may be stored in memory 634. The database may include a first pupil behavior type 1 (e.g., dilated pupils) corresponding to low BSL, a second pupil behavior type 2 corresponding to optimal BSL, a third pupil behavior type 3 corresponding to good BSL, a fourth pupil behavior type 4 corresponding to at risk BSL, a fifth pupil behavior type 5 corresponding to dangerously high BSL, a sixth pupil behavior type 6 (e.g., erratic pupil response) corresponding to possible complication, and a seventh pupil behavior type 7 (e.g., non-responsive pupils) corresponding to mortal danger BSL.

Figure 3:
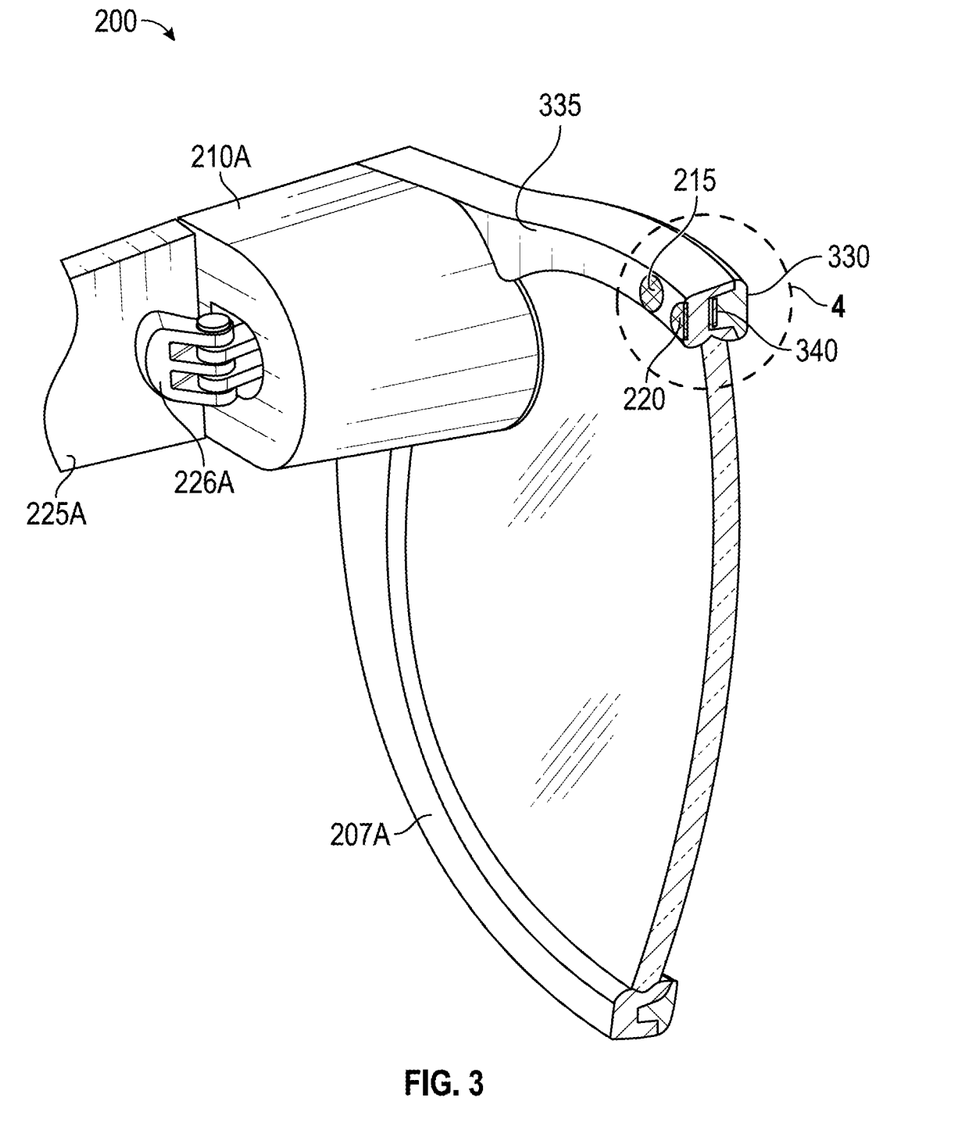
FIG. 3 is a cut away view taken through the camera and the frame of the eyewear device of FIG. 2A.

FIG. 3 depicts a rear perspective sectional view of the eyewear device of FIG. 2A illustrating an illuminator 215, a camera 220, a frame front 330, a frame back 335, and a circuit board. It can be seen that the upper portion of the left rim 207A of the frame 205 of the eyewear device 200 includes the frame front 330 and the frame back 335. The frame front 330 includes a front-facing side configured to face outwards away from the eye of the user. The frame back 335 includes a rear-facing side configured to face inwards towards the eye of the user. Opening for the illuminator 215 and the camera 220 are formed on the frame back 335.

As shown in the encircled cross-section 4 of the upper middle portion of the left rim of the frame, a circuit board, which is a flexible printed circuit board (PCB) 340, is sandwiched between the frame front 330 and the frame back 335. Also shown in further detail is the attachment of the left corner 210A to the left temple 225A via a left hinge 226A. In some examples, components of the blood sugar level sensors 213, including the illuminator 215, the camera 220, the flexible PCB 340, or other electrical connectors or contacts may be located on the left temple 225A or the left hinge 226A.

Figure 4:
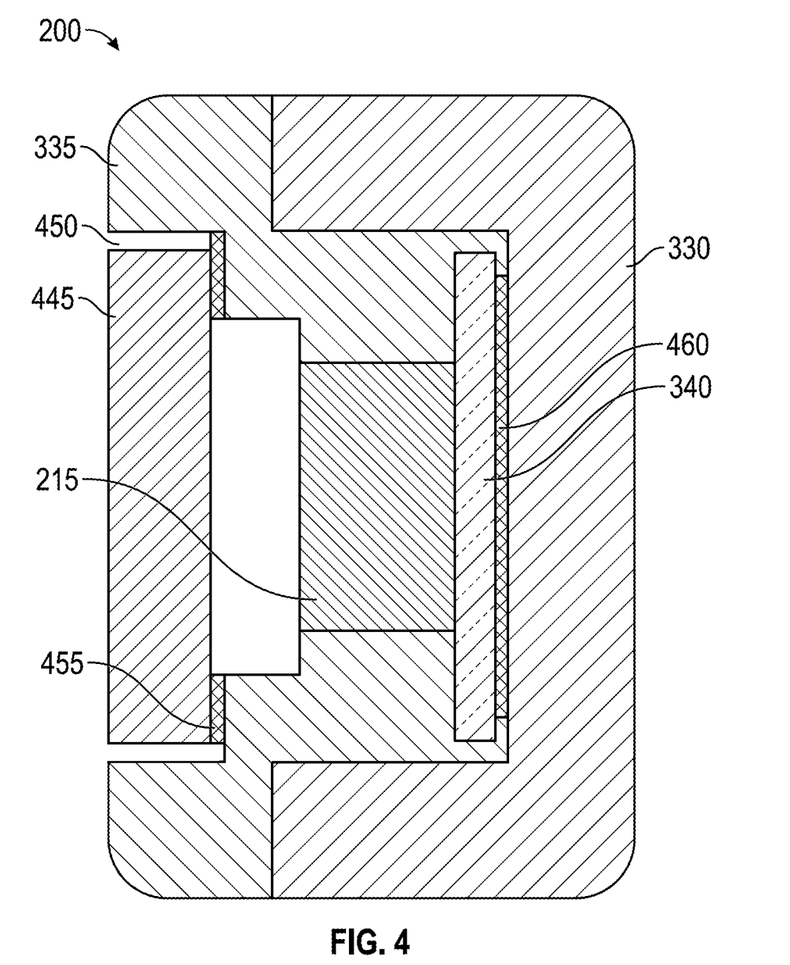
FIG. 4 is a cross-sectional view taken through the camera and the frame of the eyewear device of FIG. 3.

FIG. 4 is a cross-sectional view through the camera 220 and the frame corresponding to the encircled cross-section 4 of the eyewear device of FIG. 3. Various layers of the eyewear device 200 are visible in the cross-section of FIG. 4. As shown, the flexible PCB 340 is disposed on the frame front 330 and connected to the frame back 335. The camera 220 is disposed on the flexible PCB 340 and covered by an infrared camera cover lens 445. For example, the camera 220 is reflowed to the back of the flexible PCB 340. Reflowing attaches the camera 220 to electrical contact pad(s) formed on the back of the flexible PCB 340 by subjecting the flexible PCB 340 to controlled heat which melts a solder paste to connect the two components. In one example, reflowing is used to surface mount the camera 220 on the flexible PCB 340 and electrically connect the two components. However, it should be understood that throughholes can be used to connect leads from the camera 220 to the flexible PCB 340 via interconnects, for example.

The frame back 335 includes a camera opening 450 for the camera cover lens 445. The camera opening 450 is formed on a rear-facing side of the frame back 335 that is configured to face inwards towards the eye of the user. In the example, the flexible PCB 340 can be connected to the frame front 330 via a flexible PCB adhesive 460. The camera cover lens 445 can be connected to the frame back 335 via camera cover lens adhesive 455. The connection can be indirect via intervening components.

Figure 5:
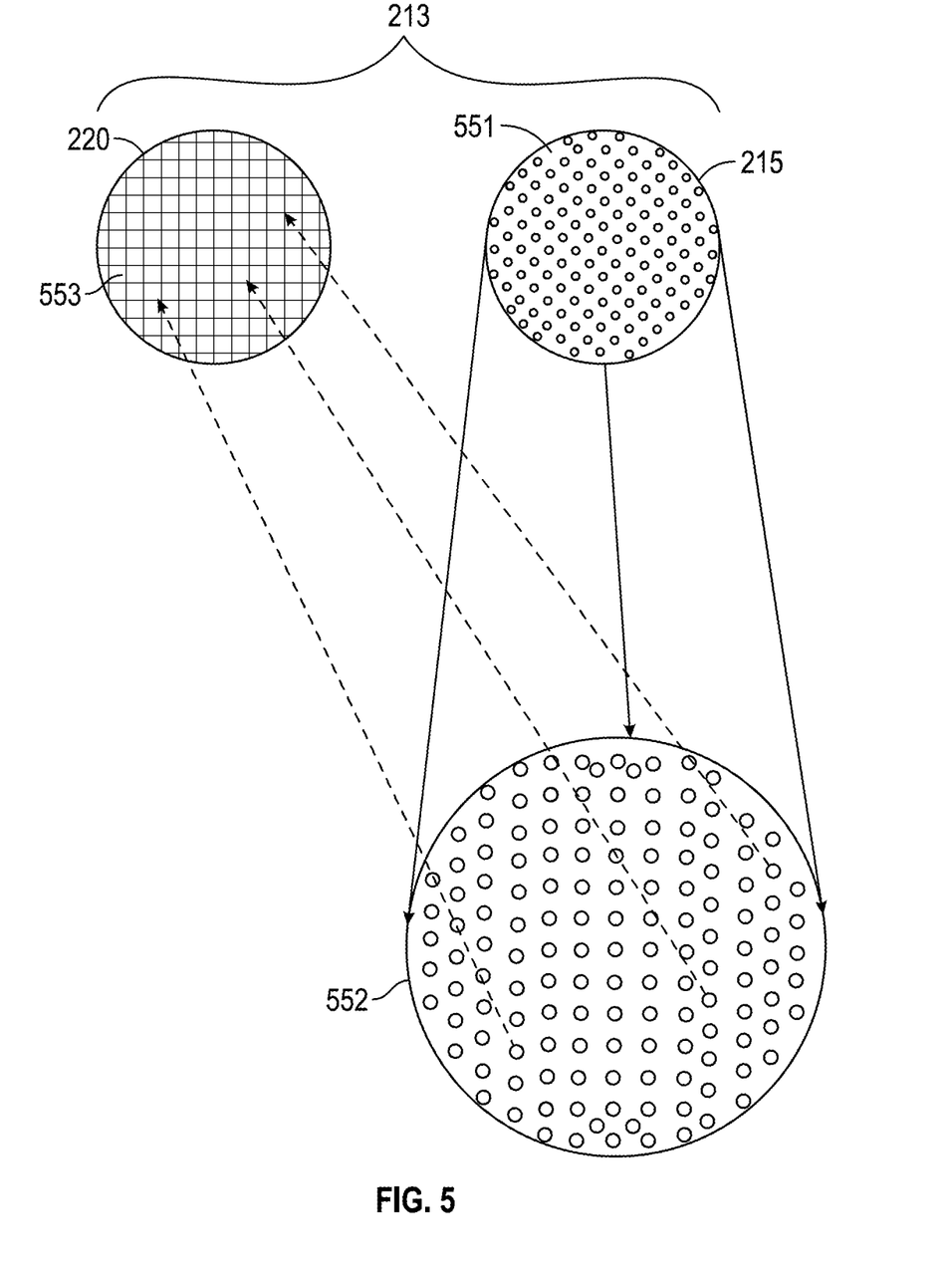
FIG. 5 in an illustrative view depicting an example of a pattern of light emitted by an illuminator of the eyewear device and reflection variations of the emitted pattern of light captured by the infrared camera of the eyewear device to track pupil behavior.

FIG. 5 depicts an example of a pattern of infrared light emitted by an illuminator 215 of the eyewear device and reflection variations of the emitted pattern of infrared light captured by the camera 220 of the eyewear device 200 to monitor the diameter of the pupil 102. FIG. 5 depicts the emitted pattern of infrared light 551 emitted by the illuminator 215 of the eyewear device in an inward facing angle of coverage towards an eye of a user to monitor pupil size.

The pattern of infrared light 551 can be a standardized matrix or beam of pixels that will outline a uniform light trace on the eye of the user (e.g., cornea, pupil, retina or iris). When the emitted pattern of infrared light 551 strikes the eye of the user 552, the camera 220 captures the reflection variations of the emitted pattern of infrared light 553, which can then be used to determine pupil diameter.

The emitted pattern of infrared light 551 may be an unperceived low-energy infrared beam that shines on the eye with a standardized path. The amount of reflection of the emitted pattern of infrared light 881 varies in different parts of the eye (e.g., retinal blood vessels absorb light more than surrounding tissue) and the iris. Camera 220 captures these reflection variations of the emitted pattern of infrared light 553, which is digitized by the components of the system. For example, the wearable device includes or is coupled to image processor, memory, and processor for digitizing the reflection variations of the emitted pattern of infrared light 553. The reflection variations of the emitted pattern of infrared light 553 can then be used to determine pupil behavior, which is compared by a pupil comparator (element 602 of FIG. 6) to pupil behavior in a blood sugar level database to determine blood sugar levels.

Figure 6:
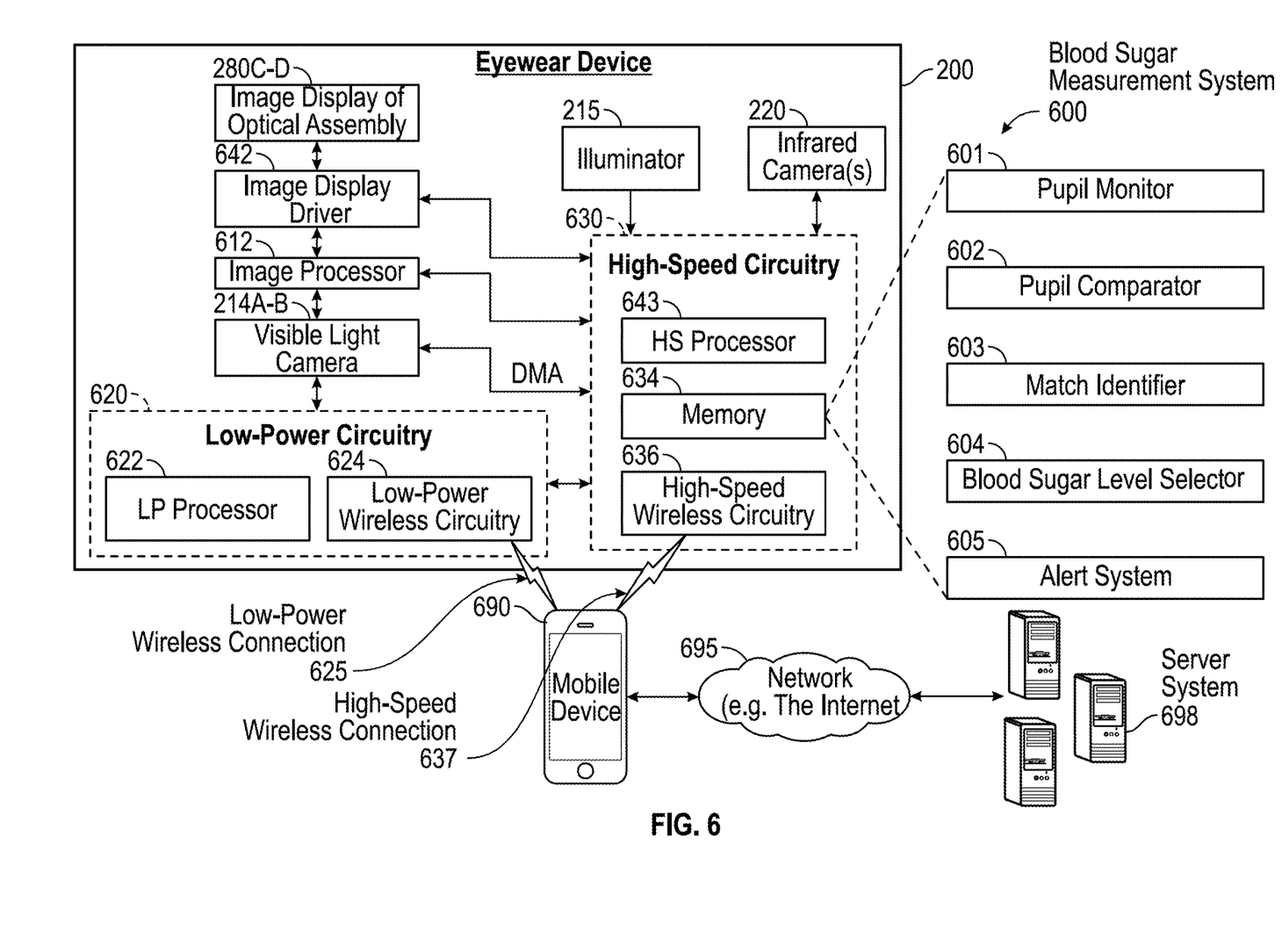
FIG. 6 is a high-level functional block diagram of an example eyewear device with blood sugar level detection, a mobile device, and a server system connected via various networks.

FIG. 6 is a high-level functional block diagram of an example blood sugar measurement system 600. The blood sugar measurement system 600 includes a wearable device, which is the eyewear device 200 with a blood sugar level sensor such as blood sugar level sensor 213 (e.g., shown as illuminator 215 and camera 220) supported by the frame of the eyewear device 200. Alternatively, the blood sugar level sensor may be a projector/sensor 232 that utilizes a waveguide within an optical assembly 280 of the eyewear device 200.

Blood sugar measurement system 600 also includes a mobile device 690 and a server system 698 connected via various networks. Mobile device 690 may be a smartphone, tablet, laptop computer, access point, or any other such device capable of connecting with eyewear device 200 using both a low-power wireless connection 625 and a high-speed wireless connection 637. Mobile device 690 is connected to server system 698 and network 695. The network 695 may include any combination of wired and wireless connections.

Eyewear device 200 includes at least two visible light cameras 214A-B (one associated with the left lateral side 170A and one associated with the right lateral side 170B). Eyewear device 200 further includes two image displays of the optical assembly 280A-B (one associated with the left lateral side 170A and one associated with the right lateral side 170B). Eyewear device 200 also includes image display driver 642, image processor 612, low-power circuitry 620, and high-speed circuitry 630.

The components shown in FIG. 6 for the eyewear device 200 are located on one or more circuit boards, for example a PCB or flexible PCB, in the temples. Alternatively, or additionally, the depicted components can be located in the corners, frames, hinges, or bridge of the eyewear device 200. Left and right visible light cameras 214A-B can include digital camera elements such as a complementary metal-oxide-semiconductor (CMOS) image sensor, charge coupled device, a lens, or any other respective visible or light capturing elements that may be used to capture data, including images of scenes with unknown objects.

As shown in FIG. 6, high-speed circuitry 630 includes high-speed processor 643, memory 634, and high-speed wireless circuitry 636. In the example, the image display driver 642 is coupled to the high-speed circuitry 630 and operated by the high-speed processor 643 in order to drive the left and right image displays of the optical assembly 280A-B. High-speed processor 643 may be any processor capable of managing high-speed communications and operation of any general computing system needed for eyewear device 200. High-speed processor 643 includes processing resources needed for managing high-speed data transfers on high-speed wireless connection 637 to a wireless local area network (WLAN) using high-speed wireless circuitry 636. In certain embodiments, the high-speed processor 643 executes an operating system such as a LINUX operating system or other such operating system of the eyewear device 200 and the operating system is stored in memory 634 for execution. In addition to any other responsibilities, the high-speed processor 643 executing a software architecture for the eyewear device 200 is used to manage data transfers with high-speed wireless circuitry 636. In certain embodiments, high-speed wireless circuitry 636 is configured to implement Institute of Electrical and Electronic Engineers (IEEE) 802.11 communication standards, also referred to herein as Wi-Fi. In other embodiments, other high-speed communications standards may be implemented by high-speed wireless circuitry 636.

Low-power wireless circuitry 624 and the high-speed wireless circuitry 636 of the eyewear device 200 can include short range transceivers (Bluetooth™) and wireless wide, local, or wide area network transceivers (e.g., cellular or WiFi). Mobile device 690, including the transceivers communicating via the low-power wireless connection 925 and high-speed wireless connection 637, may be implemented using details of the architecture of the eyewear device 200, as can other elements of network 695.

Memory 634 includes any storage device capable of storing various data and applications, including, among other things, camera data generated by the left and right visible light cameras 214A-B and the image processor 612, as well as images generated for display by the image display driver 642 on the image displays of the optical assembly 280A-B. While memory 634 is shown as integrated with high-speed circuitry 630, in other embodiments, memory 634 may be an independent standalone element of the eyewear device 200. In certain such embodiments, electrical routing lines may provide a connection through a chip that includes the high-speed processor 643 from the image processor 612 or low-power processor 622 to the memory 634. In other embodiments, the high-speed processor 643 may manage addressing of memory 634 such that the low-power processor 622 will boot the high-speed processor 643 any time that a read or write operation involving memory 634 is needed.

Server system 698 may be one or more computing devices as part of a service or network computing system, for example, that include a processor, a memory, and network communication interface to communicate over the network 695 with the mobile device 690 and eyewear device 200. Eyewear device 200 is connected with a host computer. For example, the eyewear device 200 is paired with the mobile device 690 via the high-speed wireless connection 637 or connected to the server system 698 via the network 695.

Output components of the eyewear device 200 include visual components, such as the left and right image displays of optical assembly 280A-B as described in FIGS. 2C-D (e.g., a display such as a liquid crystal display (LCD), a plasma display panel (PDP), a light emitting diode (LED) display, a projector, or a waveguide). The image displays of the optical assembly 280A-B are driven by the image display driver 642. The output components of the eyewear device 200 further include acoustic components (e.g., speakers), haptic components (e.g., a vibratory motor), other signal generators, and so forth. The input components of the eyewear device 200, the mobile device 690, and server system 698, may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instruments), tactile input components (e.g., a physical button, a touch screen that provides location and force of touches or touch gestures, or other tactile input components), audio input components (e.g., a microphone), and the like.

Eyewear device 200 may optionally include additional peripheral device elements. Such peripheral device elements may include biometric sensors, additional sensors, or display elements integrated with eyewear device 200. For example, peripheral device elements may include any I/O components including output components, motion components, position components, or any other such elements described herein.

Memory 634 includes a pupil monitor 601, a pupil comparator 602, a match identifier 603, a blood sugar level selector 604, and an alert system 605. Pupil monitor 601 configures the blood sugar measurement system 600, under control of the processor 643, to monitor pupil behavior (e.g., diameter) using, for example, a blood sugar level sensor 213 on the frame of the eyewear device 200 or a projector/sensor 232 supported within the eyewear device 200 that uses a waveguide of an optical assembly 280.

Pupil comparator 602 configures the blood sugar measurement system 600, under control of the processor 643, to compare monitored pupil behavior to known behaviors corresponding to blood sugar levels stored in a database maintained by the pupil comparator. The database may include a value(s) (e.g., pupil diameter(s)) corresponding to particular blood sugar levels or ranges, image data for single images corresponding to blood sugar levels or ranges, or image data for a series of images (representing pupil response of a period of time in response to a stimulus, for example) correspond to particular blood sugar levels or ranges. The information in the database may be general information obtained from a training set of images processed by a neural network and/or personalized information calibrated using images of the user's eye captured substantially simultaneously with blood sugar levels using more invasive techniques such as a blood reading from a finger prick, for example.

Match identifier 603 configures the blood sugar measurement system 600, under control of the processor 643, to identify a match between the monitored pupil behavior and the known behaviors corresponding to blood sugar levels stored in the database maintained by the pupil comparator 602. The match identifier 603 may be configured to identify an exact match from the database or a closest match from the database using an image recognition algorithm.

Blood sugar level selector 604 configures the blood sugar measurement system 600, under control of the processor 643, to select the blood sugar level(s) corresponding to the identified match by match identifier 603 as that blood sugar level for the user. In one example, the blood sugar level selector 604 selects a blood sugar level corresponding to the match identified by the match identifier for one sample from one eye to select the blood sugar level for the user. In another example, the blood sugar level selector 604 selects blood sugar levels corresponding to the match identified by the match identifier for one sample from each of both eyes and averages the results to select the blood sugar level for the user. In another example, the blood sugar level selector 604 selects blood sugar levels corresponding to the match identified by the match identifier for multiple samples from one or both eyes and averages the results to select the blood sugar level for the user.

Alert system 605 configures the blood sugar measurement system 600, under control of the processor 643, to alert a user and/or a third party of blood sugar levels. Alert system 605 configures processor 643, for example, to display a warning and/or a blood sugar level to the wearer via image display driver 642 and image display 280. Alert system 605 may additionally configure processor 643 to send a warning and/or a blood sugar level to a third party such as a parent or other caregiver via a wireless connection 625/637 and network 695.

Figure 7:
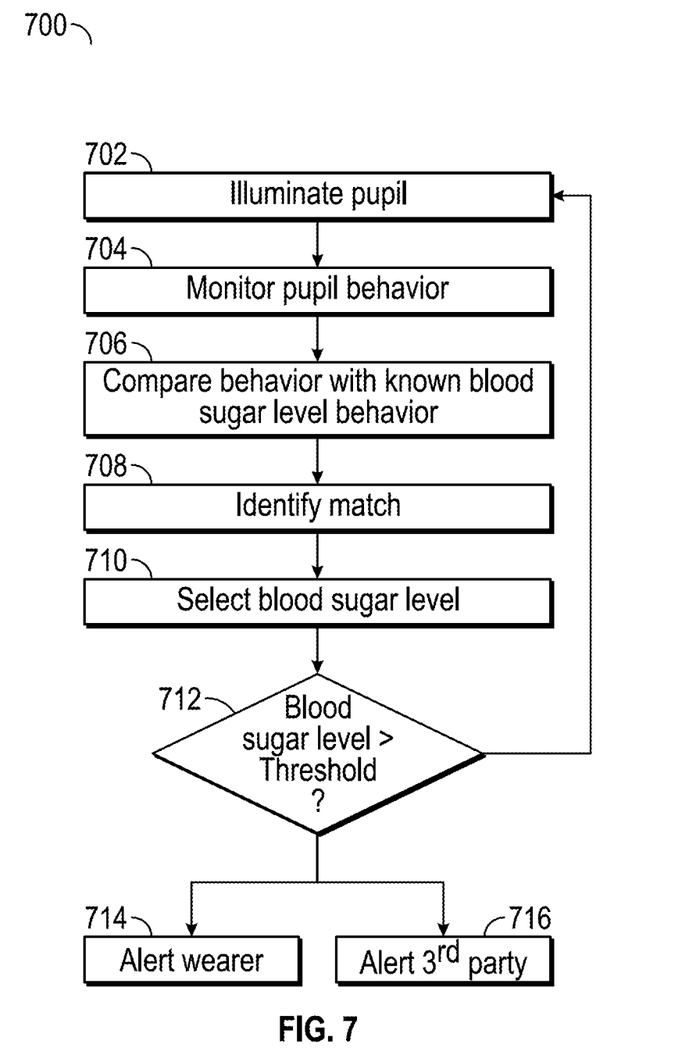
FIG. 7 is a flowchart of the operation of the eyewear device to implement blood sugar level detection.

FIG. 7 is a flowchart 700 of the operation of the eyewear device 200 to implement blood sugar level detection. Although the steps are described with reference to the eyewear device 200, as described herein, other implementations of the steps described, for other types of devices, will be understood by one of skill in the art from the description herein. Additionally, it is contemplated that one or more of the steps shown in FIG. 7 and described herein may be omitted, performed simultaneously and/or in a series, performed in an order other than illustrated and described, and/or performed in conjunction with additional steps.

At block 702, illuminate the eye of the user. In an example, the processor 643 prompts the illuminator 215 to illuminate the eye with a flash(es) of visible light. In another example, the processor 643 prompts the illuminator 215 to illuminate the eye with near IR light to facilitate collection of an IR image from reflections. In other examples, this step may be omitted, e.g., when light is directed into the pupil via a waveguide or the camera collects reflections from ambient light reflected by the eye 100.

At block 704, monitor pupil behavior. The processor 643 monitors pupil behavior using pupil monitor 601. In an example, processor 643 monitors pupil behavior using blood sugar level sensor 213 by processing an image(s) collected by camera 220, e.g., in response to reflection of light from illuminator 215 by the surface of the eye. In another example, processor 643 monitors pupil behavior using projector/sensor 232 and a waveguide within an optical element 280 by processing an image(s) obtained by sensor 232 resulting from reflections of an optical beam creating a point source image on the retina 110 of the eye 100.

At blocks 706 and 708, compare pupil behavior with known blood sugar level behavior and identify a match, respectively. The processor 643 compares monitored pupil behavior to known behaviors corresponding to blood sugar levels stored in a database maintained by the pupil comparator 602. The processor 643 may compare the pupil behavior to identify an exact match or a closest match using an image recognition algorithm, for example.

At block 710, select a blood sugar level for the user. The processor 643 selects the blood sugar level(s) corresponding to the identified match. For example, if the processor 643 identifies a match with a first type of pupil behavior (see Table 1), the processor 643 selects a blood sugar level of less than 65 mg/dl (e.g., <65 65 mg/dl). In one example, the selected blood sugar level corresponds to the match identified by the match identifier for one sample from one eye. In another example, the selected blood sugar level corresponds to an average for a match identified for one sample from each of both eyes. In another example, the selected blood sugar level corresponds to an average for a match identified for multiple samples from one or both eyes.

At decision block 712, determine if the blood sugar level crosses a threshold. If the threshold is crossed, processing may proceed at blocks 714 and 716. The processor 643 may determine if the blood sugar level crosses an upper threshold (e.g., is greater than the threshold as indicated in block 712) by comparing the selected blood sugar level to a predefined threshold. For example, if the threshold is 171 mg/dl and the selected blood sugar level is 175 (indicating a dangerously high blood sugar level; Table 1), the processor 643 may alert the wearer at block 714 and a third party at block 716. Likewise, if the blood sugar level crosses a lower threshold (e.g., is less than the threshold) by comparting the selected blood sugar level to a different predefined threshold. For example, if the threshold is 65 mg/dl and the selected blood sugar level is 60 (indicating a low blood sugar level; Table 1), the processor 643 may alert the wearer at block 714 and a third party at block 716.

The threshold levels may be different for alerting the wearer versus alerting a third party. For example, the threshold may be 171 mg/dl (above which indicates a dangerously high blood sugar level; Table 1) for alerting the user at block 714 and the threshold may be 136 mg/dl (above which indicates a risky high blood sugar level; Table 1) for alerting a third party at block 716.

In another example, the blood sugar level and/or alert is always presented to a user and/or a third party with processing proceeding to block 714 and/or block 716 regardless of blood sugar level. In accordance with this example, block 712 may be omitted.

At block 714, alert the user of their blood sugar level. Processor 643 alerts the user by, for example, displaying the blood sugar level or a warning (associated with the blood sugar level; e.g., high/low) to the user via the image display driver 642 and the image display 280. The warning may be message (e.g., low blood sugar) and/or an indicator (e.g., flashing red light).

At block 716, alert a third party of the user's blood sugar levels. Processor 643 alerts the third party, for example, by sending a blood sugar level and/or a warning (associated with the blood sugar level) to a third party such as a parent or other caregiver via a wireless connection 625/637 and network 695.

Any of the blood sugar level detection functionality described herein for the eyewear device 200, mobile device 690, and server system 698 can be embodied in one more applications as described previously. According to some embodiments, "function," "functions," "application," "applications," "instruction," "instructions," or "programming" are program(s) that execute functions defined in the programs. Various programming languages can be employed to create one or more of the applications, structured in a variety of manners, such as object-oriented programming languages (e.g., Objective-C, Java, or C++) or procedural programming languages (e.g., C or assembly language). In a specific example, a third party application (e.g., an application developed using the ANDROID™ or IOS™ software development kit (SDK) by an entity other than the vendor of the particular platform) may be mobile software running on a mobile operating system such as IOS™, ANDROID™ WINDOWS® Phone, or another mobile operating systems. In this example, the third-party application can invoke API calls provided by the operating system to facilitate functionality described herein.

Hence, a machine-readable medium may take many forms of tangible storage medium. Non-volatile storage media include, for example, optical or magnetic disks, such as any of the storage devices in any computer(s) or the like, such as may be used to implement the client device, media gateway, transcoder, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. An eyewear device including:
a frame supporting a display;
a camera supported by the eyewear device and configured to detect a pupil of an eye of a user;
an illuminator configured to emit a flash of light towards the pupil, wherein the illuminator is separate from the camera;

a memory;
a processor having access to the camera and the memory; and
programming in the memory, wherein execution of the programming by the processor configures the eyewear device to perform functions, including functions to:
monitor behavior of the pupil with the camera and the illuminator;
compare the monitored behavior with known blood sugar level behaviors, each known blood sugar level behavior corresponding to a different blood sugar level;
identify a match responsive to the comparison between the monitored behavior and one of the known blood sugar level behaviors corresponding to a particular blood sugar level;
select the particular blood sugar level as a blood sugar level of the user;
compare the blood sugar level to a threshold; and
present on the display an alert to the user if the blood sugar level crosses the threshold.

2. The eyewear device of claim 1, wherein execution of the programming by the processor configures the eyewear device to perform further functions, including functions to:
illuminate the pupil of the eye with a flash of light, wherein the function to monitor the behavior of the pupil of the eye with the camera monitors the pupil behavior in response to the flash of the light.

3. The eyewear device of claim 1, wherein the illuminator is a visible light emitting diode (LED).

4. The eyewear device of claim 3, wherein the camera is an infrared (IR) imager.

5. The eyewear device of claim 1, wherein the camera is a visible spectrum camera.

6. The eyewear device of claim 1, wherein the frame includes a first rim configured to support a first lens and a second rim and wherein the camera is positioned on the first rim facing the eye, the eyewear device further comprising:
another camera positioned on the second rim facing another eye of the user;
wherein execution of the programming by the processor configures the eyewear device to perform further functions, including functions to:
monitor behavior of another pupil of the other eye with the other camera;
compare the monitored behavior with the known blood sugar level behaviors;
identify a match responsive to the comparison between the monitored behavior of the other pupil and one of the known blood sugar level behaviors corresponding to a particular blood sugar level;
select the particular blood sugar level as another blood sugar level of the user; and
average the blood sugar level and the other blood sugar level to obtain an averaged blood sugar level.

7. The eyewear device of claim 6, wherein the first lens includes a waveguide extending from an outer region of the lens to a central region of the first lens and wherein the camera is supported by the frame and is coupled to the waveguide in the outer region, the camera receiving light from the pupil passing from the central region to the outer region.

8. The eyewear device of claim 7, wherein the illuminator is supported by the frame and is coupled to the waveguide in the outer region, the illuminator passing light into the waveguide at the outer region for delivery to the pupil at the central region.

9. The eyewear device of claim 1, further comprising:
a notification device supported by the eyewear device;
wherein execution of the programming by the processor configures the eyewear device to perform further functions, including functions to:
produce an alert via the notification device when the blood sugar level crosses the threshold.

10. The eyewear device of claim 1, wherein execution of the programming by the processor configures the eyewear device to perform further functions, including functions to:
display the blood sugar level or a representation of the blood sugar level via the display when the blood sugar level crosses the threshold.

11. The eyewear device of claim 1, further comprising:
a transmitter supported by the eyewear device;
wherein execution of the programming by the processor configures the eyewear device to perform further functions, including functions to:
transmit an alert to a third party via the transmitter when the blood sugar level crosses the threshold.

12. A method for use with an eyewear device having a frame supporting a display, the method comprising:
monitoring behavior of a pupil of an eye of a user with a camera and an illuminator, wherein the illuminator is separate from the camera and configured to emit a flash of light that enables the camera to monitor pupil behavior;
comparing the monitored behavior with known blood sugar level behaviors, each known blood sugar level behavior corresponding to a different blood sugar level;
identifying a match responsive to the comparison between the monitored behavior and one of the known blood sugar level behaviors corresponding to a particular blood sugar level;
selecting the particular blood sugar level as a blood sugar level of the user;
comparing the blood sugar level to a threshold; and
present on the display an alert to the user when the blood sugar level crosses the threshold.

13. The method of claim 12, further comprising:
monitoring behavior of another pupil of another eye of the user with another camera;
comparing the monitored behavior with the known blood sugar level behaviors;
identifying a match responsive to the comparison between the monitored behavior of the other pupil and one of the known blood sugar level behaviors corresponding to a particular blood sugar level;
selecting the particular blood sugar level as another blood sugar level of the user; and
averaging the blood sugar level and the other blood sugar level to obtain an averaged blood sugar level.

14. The method of claim 12, further comprising:
producing an alert via a notification device when the blood sugar level crosses the threshold.

15. The method of claim 12, further comprising:
displaying the blood sugar level or a representation of the blood sugar level as an image overlay via the display when the blood sugar level crosses the threshold.

16. The method of claim 12, further comprising:
comparing the blood sugar level to a threshold; and
transmitting an alert to a third party via a transmitter when the blood sugar level crosses the threshold.

17. A non-transitory computer-readable medium for use with and eyewear device having a frame supporting a display, the non-transitory computer-readable medium including programming, wherein execution of the programming by a processor of the eyewear device configures the eyewear device to perform functions, including functions to:
- monitor behavior of a pupil of an eye of a user with a camera and an illuminator, wherein the illuminator is configured to emit a flash of light to illuminate the pupil that enables the camera to monitor pupil behavior, wherein the illuminator is separate from the camera;
- compare the monitored behavior with known blood sugar level behaviors, each known blood sugar level behavior corresponding to a different blood sugar level;
- identify a match responsive to the comparison between the monitored behavior and one of the known blood sugar level behaviors corresponding to a particular blood sugar level;
- select the particular blood sugar level as a blood sugar level of the user;
- compare the blood sugar level to a threshold; and
- present on the display an alert to the user when the blood sugar level crosses the threshold.

18. The non-transitory computer-readable medium of claim 17, wherein execution of the programming by the processor of the eyewear device configures the eyewear device to perform further functions, including functions to:
- displaying the blood sugar level or a representation of the blood sugar level as an image overlay via the display when the blood sugar level crosses the threshold.

19. The non-transitory computer-readable medium of claim 17, wherein execution of the programming by the processor of the eyewear device configures the eyewear device to perform further functions, including functions to:
- producing an alert via a notification device when the blood sugar level crosses the threshold.

20. The non-transitory computer-readable medium of claim 17, wherein execution of the programming by the processor of the eyewear device configures the eyewear device to perform further functions, including functions to:
- transmitting an alert to a third party via a transmitter when the blood sugar level crosses the threshold.

\* \* \* \* \*